(12) United States Patent
Feriani et al.

(10) Patent No.: US 8,011,599 B2
(45) Date of Patent: Sep. 6, 2011

(54) METHOD AND DEVICE FOR NEBULISING HIGH-VISCOSITY LIQUIDS WITH MINIMAL FALLBACK

(75) Inventors: Amir Feriani, Auvernier (CH); Joseph Hess, Bevaix (CH)

(73) Assignee: EP Systems SA Microflow Division, Neuchâtel (CH)

( * ) Notice: Subject to any disclaimer, the term of this patent is extended or adjusted under 35 U.S.C. 154(b) by 32 days.

(21) Appl. No.: 12/403,066

(22) Filed: Mar. 12, 2009

(65) Prior Publication Data

US 2009/0230208 A1    Sep. 17, 2009

(30) Foreign Application Priority Data

Mar. 12, 2008 (EP) ..................... 08004580

(51) Int. Cl.
*B05B 17/06* (2006.01)
*B05B 1/08* (2006.01)
*B05B 12/10* (2006.01)

(52) U.S. Cl. .................. 239/4; 239/69; 239/70; 239/75; 239/102.2

(58) Field of Classification Search ................ 239/4, 67, 239/69, 70, 71, 75, 102.1, 102.2; 128/200.14, 128/200.16
See application file for complete search history.

(56) References Cited

U.S. PATENT DOCUMENTS

| | | |
|---|---|---|
| 4,085,893 A | 4/1978 | Durley, III |
| 5,173,274 A | 12/1992 | Owen |
| 5,601,235 A | 2/1997 | Booker et al. |
| 5,894,001 A | 4/1999 | Hitzler et al. |
| 6,793,149 B2 | 9/2004 | Schramm et al. |
| 7,070,121 B2 | 7/2006 | Schramm et al. |
| 2002/0129813 A1 | 9/2002 | Litherland et al. |
| 2003/0146292 A1 | 8/2003 | Schramm et al. |
| 2004/0144853 A1* | 7/2004 | Helf et al. .......... 239/4 |
| 2005/0037945 A1 | 2/2005 | Gygax et al. |
| 2005/0279854 A1* | 12/2005 | Martens et al. ......... 239/44 |

FOREIGN PATENT DOCUMENTS

| | | |
|---|---|---|
| EP | 1 129 741 A2 | 9/2001 |
| EP | 2 047 914 A1 | 4/2009 |
| WO | 00/47335 A1 | 8/2000 |
| WO | 2007/054920 A1 | 5/2007 |
| WO | 2008/015394 A1 | 2/2008 |
| WO | 2008/039393 A | 4/2008 |

OTHER PUBLICATIONS

International Search Report, issued in corresponding application No. EP 08 004580, completed Jun. 26, 2008, mailed Jul. 3, 2008.
Email from Elson Silva, "Applied Hydrology to Fluidic Devices," Understanding Hydrology in the Patenting System, dated May 31, 2010, pp. 1-8.

* cited by examiner

*Primary Examiner* — Darren W Gorman
(74) *Attorney, Agent, or Firm* — Griffin & Szipl, P.C.

(57) ABSTRACT

A method of controlling evaporation of droplet cloud resulting from nebulization of a liquid expelled from a liquid droplet spray device is disclosed, wherein the liquid droplet spray device comprises a reservoir containing liquid, a perforate membrane plate, a fluid interface for feeding liquid from the reservoir to the membrane plate, an ultrasound generating mechanism for acting on the supplied liquid to cause it to be expelled as a spray of droplets through orifices of the membrane plate, and an electronic control device for controlling activation of the ultrasound generating mechanism.

9 Claims, 1 Drawing Sheet

METHOD AND DEVICE FOR NEBULISING HIGH-VISCOSITY LIQUIDS WITH MINIMAL FALLBACK

This application claims priority from European Patent Application No. 08 044 580.0, filed Mar. 12, 2008, the entire disclosure of which is incorporated herein by reference.

FIELD OF THE INVENTION

The present invention relates to the dispersal of liquids having a relatively high-viscosity, such as insecticides and fragrance solutions, and gel or lotion-like formulations by ejecting a cloud or mist of small droplets of the liquid from a liquid droplet spray device into the atmosphere and allowing the droplets to evaporate well before they fall back through the atmosphere.

BACKGROUND OF THE INVENTION

Such liquids may be for example fragrance compositions such as described in US 2005/0037945, or insecticides or still other liquids having a relatively high viscosity.

Such liquid droplet spray devices are also sometimes called piezoelectric spray devices, aerosol generators, nebulizers and the like. They normally contain a nozzle body on a support part, in particular, a nozzle body of a liquid droplet spray device which dispenses a liquid substance as a liquid droplet spray. They further consist of a piezoelectric actuator used as vibrating means for causing the liquid to vibrate so as to be accelerated and expelled as droplets. They further consist of elements such as a liquid space, liquid feed and fluid interface linked to a reservoir, a reservoir as well as electrical connections between the ultrasound generating means and a corresponding electronic circuitry. The liquid may be for example an ambient fragrance, a perfume, an insecticide, an aromatherapy essence, a liquid pharmaceutical formulation, aqueous based liquids and flammable or combustible liquids.

Such nozzle bodies are sometimes called aperture plates, nozzle arrays, dosing aperture, orifice plate, vibratable membrane member, dosing aperture arrangement, aerosol generator and the like. Such terms are hence to be understood as being interchangeable throughout the present document.

In fact such nozzle bodies and droplet spray devices are well known. For example see the document EP 1 129 741 in the name of the present Applicant. This document describes a liquid droplet spray device having a top substrate formed of a main body and of a nozzle body. The nozzle body contains a nozzle array of liquid droplet outlet means allowing a liquid substance contained in the liquid droplet spray device to exit the device, in this case as a spray of droplets. A piezoelectric actuator is used to cause the liquid to undergo a vibration so as to generate the droplet spray.

It is well known to disperse fragrances and insecticides into the atmosphere by such device to form a mist or cloud of small droplets of a liquid substance containing the fragrance or insecticide and to eject the mist or cloud into the atmosphere in the form of minute liquid droplets. As the mist or cloud settles, the fragrance or insecticide evaporates from the droplets. Examples of devices for doing this are shown in U.S. Pat. No. 4,085,893, U.S. Pat. No. 5,173,274, U.S. Pat. No. 5,601,235 and U.S. Pat. No. 5,894,001. In general these devices supply the liquid fragrance or insecticide to a vibrating atomization plate which, due to its vibrations, breaks up the liquid into fine droplets and ejects them upwardly in the form of a mist or a cloud. As the droplets fall back down, the fragrance or insecticide evaporates from the droplets and disperses into the atmosphere.

Document WO 2008/015394 describes a spray device without an atomiser plate, but instead uses a wick fixedly attached to a vibrating element. When the vibrating element is activated, the wick will vibrate together with the vibrating element so that any liquid absorbed by the wick will be dispersed therefrom. Such device may avoid clogging, due to the absence of an atomiser plate, but the disclosure is totally silent about fallback.

Document WO 00/47335 describes another example of such a device, and a corresponding method for dispensing liquids of relatively low viscosity. The described device uses a dome-shaped vibrating orifice plate that is actuated by a piezoelectric vibrating element to vibrate the plate. Once the plate vibrates, liquid is supplied to the plate by capillary action so as to be expelled there from as a spray of droplets. As described in this document, liquids having a viscosity of less than 5 centipoises may be used, but at higher viscosity, the device stops functioning.

A problem occurs in the operation of these known devices in that there is no means to be sure that all of the liquid which is ejected will indeed evaporate before the droplets fall back onto surrounding surfaces. As a result, an often destructive liquid residue of unevaporated liquid builds up on these surfaces. This problem is particularly difficult where the liquid to be ejected is a fragrance or an insecticide having a relatively high viscosity. This is because fragrance and insecticide compositions are generally quite complex; and there has been no way to know in advance that a particular composition will fully evaporate when subjected to atomization in a vibrating plate atomizer.

Document WO 2007/054920 describes a further example of such device having a vibratable atomizer plate. Here, an air disturbance generator, such as a fan, is proposed to increase the ability of the ejected mist of droplets to remain airborne so as to increase the time allowing for increased vaporization of the droplet mist. The ejected droplets are compositions having lower and higher volatile components, and only the highly volatile components remain airborne, but the other components fall back down onto the surrounding surface. Further, a fan constitutes an additional component that needs to be placed correctly and adds to the constructional costs of the device.

A solution has been proposed in view of these problems by analysing the vapour pressure of the components of the sprayed liquid. Indeed, according to U.S. Pat. No. 6,793,149 and U.S. Pat. No. 7,070,121, when liquid compositions are broken up into small droplets and ejected into the atmosphere above a surrounding surface, such as a tabletop, for example, the ability of those droplets to become fully evaporated before they fall back onto the surrounding surface, does not depend on the vapour pressure of the liquid composition itself. Instead the ability of the droplets to evaporate depends upon the vapour pressures of the individual components of the liquid composition. This document thus describes a method of nebulising a multi-component liquid solution having a high-viscosity, such as a multi-component liquid insecticide or a perfume in a manner such that the amount of liquid deposited on adjacent surfaces is minimized. The liquid solution comprises a plurality of components having respective vapour pressures. The described method is based on the discovery that the vapour pressure of the lowest vapour pressure component of the liquid composition must be such that this component will evaporate before the liquid droplet containing this component reaches the surrounding surface.

However, according to this same document, the composition of liquids is not always exactly known. Where liquid compositions, such as fragrances or insecticides, comprise large numbers of components, it is often not practical to ascertain the vapour pressures of each of the individual components in order to determine the evaporation characteristics of nebulised droplets of the liquid. Further, often, the liquid components themselves and their respective concentrations are not known because the fragrance or insecticide is maintained by the supplier as a trade secret.

In such cases, it is thus impossible to use the described method.

It is, therefore, an object of the present invention to provide an innovative method and liquid droplet spray device for controlling the evaporation of the droplet cloud resulting from nebulising a liquid that overcome the inconveniences and limitations presented by the prior art documents, and that allow to minimise the fall back for liquids such as fragrances or the like.

SUMMARY OF THE INVENTION

Thus, the present invention concerns a method and liquid droplet spray device in accordance with various embodiments. For example, in accordance with a first embodiment of the present invention, a method of controlling the evaporation of the droplets of a liquid nebulised as a spray of droplets from a liquid droplet spray device is provided, wherein the liquid droplet spray device comprises a reservoir (3) for containing the liquid, a perforate membrane plate (5), fluid interface means (9) for feeding the liquid from the reservoir (3) to the membrane plate (5), ultrasound generating means (13) for acting on the supplied liquid to cause it to be expelled as a spray of droplets through orifices (7) of the membrane plate (5) and electronic control means (15) for controlling the activation of the ultrasound generating means (13), and the method includes the steps of: (a) providing the liquid droplet spray device; (b) supplying the liquid to a space (12) below the perforated membrane plate (5); (c) providing a pulsed driving signal having a period T for activating the ultrasound generating means (13); (d) activating the ultrasound generating means (13) for a period of time $T_{on}$ so as to cause the spray of droplets to be expelled at a maximum spray cloud height, $T_{on}$ consisting of $T_{ona}$ and $T_{onb}$; and (e) de-activating the ultrasound generating means for a period of time $T_{off}$, where $T_{off} \geq T_{on}+T_{evap}$, wherein $T_{evap}$ is the time that is required for the sprayed cloud of a given liquid produced during $T_{on}$ to fully evaporate, and wherein $T_{ona}$ is the time required to ultrasonically energise the liquid, $T_{onb}$ is the time to spray the liquid, and $T_{ona}$ lasts from less than tens of milliseconds to several seconds, whereby the amount of unevaporated liquid that falls back on a surface surrounding the liquid droplet spray device is minimised.

In accordance with a second embodiment of the present invention, the first embodiment is further modified so that $T_{off} > T_{on}+T_{evap}$. In accordance with a third embodiment of the present invention, the first embodiment is modified to further include the step of (f) providing a fan, wherein the fan is activated for a time $T_{onf}$ and where $T_{onf}$ starts several milliseconds before $T_{onb}$ and lasts several milliseconds longer than $T_{onb}$.

In accordance with a fourth embodiment of the present invention, a liquid droplet spray device for nebulising a liquid expelled from the liquid droplet spray device is provided, wherein the device includes: (a) a reservoir (3) for containing the liquid; (b) a perforate membrane plate (5); (c) a space (12) for containing the liquid to be expelled, the space being positioned adjacent the membrane plate (5) and arranged to receive liquid from the reservoir (3); (d) fluid interface means (9) for feeding the liquid from the reservoir (3) to the space (12); (e) ultrasound generating means (13) for acting on the supplied liquid to cause it to be expelled as a spray of droplets through orifices (7) of the membrane plate (5); and (f) electronic control means (15) for controlling the activation of the ultrasound generating means (13), wherein the electronic control means (15) is configured to drive the ultrasound generating means (13) with a pulsed driving signal having a period T, wherein the electronic control means (15) is configured to activate the ultrasound generating means (13) for a period of time $T_{on}$ so as to cause a spray of droplets to be expelled at a maximum spray cloud height, $T_{on}$ consisting of $T_{ona}$ and $T_{onb}$, wherein the electronic control means (15) is configured to not to activate the ultrasound generating means (13) for a period of time $T_{off}$, where $T_{off} \geq T_{on}+T_{evap}$, wherein $T_{evap}$ is the time that is required for the sprayed cloud of a given liquid produced during $T_{on}$ to fully evaporate, and wherein $T_{ona}$ is the time required to ultrasonically energise the liquid, $T_{onb}$ is the time to spray the liquid, and $T_{ona}$ lasts from less than tens of milliseconds to several seconds, whereby the amount of unevaporated liquid that falls back on a surface surrounding the liquid droplet spray device is minimised.

In accordance with a fifth embodiment of the present invention, the fourth embodiment is modified so that $T_{off} > T_{on}+T_{evap}$. In accordance with a sixth embodiment of the present invention, the fourth embodiment is modified so that the electronic control means (15) includes memory means for storing fabrication parameters of the ultrasound generating means (13). In accordance with a seventh embodiment of the present invention, the fourth embodiment is modified so that the memory means further stores external parameters comprising ranges of viscosities of liquids at specific temperatures to be used with the liquid droplet spray device. In accordance with an eighth embodiment of the present invention, the fourth embodiment is modified so that the fluid interface means are sized in such a way that their capillary action for a given viscosity is such that the space (12) is filled in an optimal way in order to further reduce fall out. In accordance with a ninth embodiment of the present invention, the fourth embodiment is modified so as to further include a fan, wherein the fan is arranged to be activated for a time $T_{onf}$ where $T_{onf}$ starts several milliseconds before $T_{onb}$ and lasts several milliseconds longer than $T_{onb}$.

Thanks to the features of the method and liquid droplet spray device according to the present invention, it is possible to reliably minimise the fall back for liquids of relatively high-viscosity.

The method works independently of the vapour pressure of liquid components, so that even for unknown compositions of a liquid substance, it is possible to avoid fallback on surrounding surfaces.

In fact, liquid droplets are ejected sufficiently high to avoid fallback, i.e. the droplets fully evaporate well before they may fall back close to the surface near the spray device. Further, the present invention ejects the droplets in a controlled manner to avoid that a too high-density cloud of droplets is created. By having a relatively low-density cloud, the fallback can be further minimised.

Indeed, in the liquid droplet spray device, the ultrasound generating means, such as a piezoelectric actuator, is controlled by electronic means that control the turning on and off of the actuator, thereby effectively controlling the spraying.

BRIEF DESCRIPTION OF THE DRAWINGS

Other features and advantages of the method and liquid droplet spray device according to the present invention will become clear from reading the following description, which is given solely by way of a non-limitative example thereby referring to the attached drawings in which.

DETAILED DESCRIPTION OF THE INVENTION

A general overview of flow principles is first briefly explained.

It is known that the flow rate of ejected liquids depends on the diameter of the liquid droplets as well as on the density of outlet nozzles through which the liquid is ejected. This diameter directly depends on the diameter of an outlet nozzle through which the liquid passes to be ejected as a spray. Further, the flow rate is inversely proportional to the viscosity of the liquid and the pressure drop across the outlet nozzles. Thus, persons skilled in the art will readily recognise that the physical dimensions of the atomizer, in particular its outlet means, will be matched to the physical properties of the liquid to be expelled to ensure efficient spraying of the liquid.

For example, all other nozzle dimensions remaining equal, the diameter D0 of an outlet nozzle is 4 µm, and, the diameter D1 is 4.5 µm. For a given liquid viscosity of 4 cp we obtain the following:

$$Qv_1(4.5) = (1+x)QV_0(4)$$

Experimental measurements have shown that x is 0.3 in this case, so that the flow rate increases by 30%, whilst the diameter size has increased from 4 to 4.5 µm, i.e. by 12.5% for a same density of outlet nozzles. The size of the expelled droplets has increased by about 10%.

The Dv50 (as measured in a well-known manner for example on a Malvern Mastersizer) increased by 3.3% which does not have any impact on the fall-back, i.e. on the amount of droplets that do not evaporate but fall back onto the surface surrounding the spray device.

An example of a preferred embodiment will now be described while referring to FIG. 1.

Figure 1:
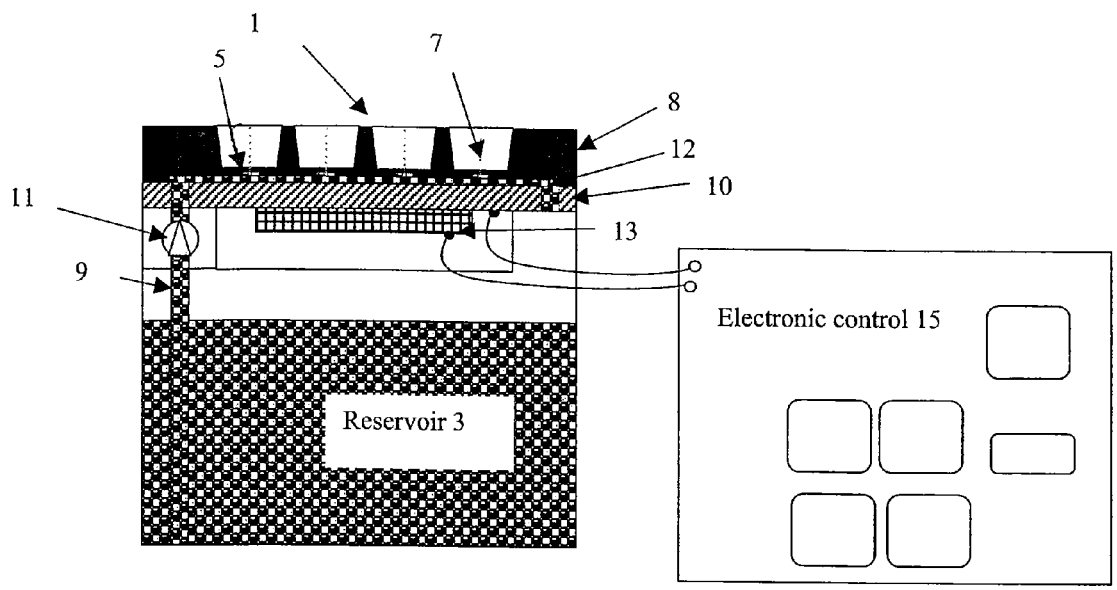
FIG. 1 shows an example of a liquid droplet spray device according to the present invention.

FIG. 1 show a schematic representation of a liquid droplet spray device according to the present invention. However, the shown structure is merely an example of a suitable device. Other structures, known as such in the art, may be used instead, as the main aspect of this present invention is the controlling of the ejection of droplets from the device. Thus, in the example, the liquid droplet spray device 1 comprises a reservoir 3 for containing liquid to be expelled. Such reservoir may be internal to the device, or external, and may be a disposable reservoir or not. Such reservoir may be a bottle, or a collapsible bag, or any other suitable liquid recipient.

The device has a perforated membrane plate 5 having a plurality of outlet means 7 through which the liquid is to be expelled as a spray of droplets. In this example, the perforated membrane plate is included in a first substrate 8 arranged above a second substrate 10, thereby enclosing a space 12, or pressure chamber, for containing liquid to be expelled. Other arrangements may be used instead, and are well known in the art. Important here is that liquid is provided to the space 12 adjacent to a perforated membrane plate so as to allow for ejection of the liquid through the nozzles of the plate to obtain a mist of expelled droplets.

Thus, liquid supply means 9 are provided for feeding liquid from the reservoir by capillary action to the space and thus the membrane plate. In this example, an optional valve 11 is further shown controlling the feed from the reservoir to the membrane plate. In an alternative, wicking means may be provided for feeding the liquid from the reservoir, in a manner well known in the art.

The liquid supply means 9 are preferably sized in such a way that their capillary action for a given viscosity is such that space 12 is filled in an optimal way in order to avoid fall out. Partial filling because of insufficient capillarity would leave room for air inclusions in space 12, hence reducing the efficiency of ultrasonic energy transmitted to the liquid by ultrasound generating means 13 and thus reducing spray height which may result in fall-out. For this reason, for a given viscosity, the capillarity lift height of the liquid supply means 9 need to improve on the liquid supply capability furnished by wicking means and the reservoir.

Ultrasound generating means 13 are further provided and arranged to act on the liquid so that the liquid undergoes a vibration due to which it is expelled through the nozzles of the perforated membrane plate. For example, a piezoelectric element may be used as the ultrasound generating means. In this example, the ultrasound generating means are shown to be below the spray device, but such means may be arranged on the top surface, near the perforated membrane plate, as is known as such in the art.

Electronic control means 15 are further provided for controlling the actuation of the ultrasound generating means. Such electronic control means may comprise an analogue circuit, a microcontroller, a timer and the like components in suitable combinations. A driving signal generator may also be included, or such may be provided separately. By controlling the "on" and "off" time, respectively called $T_{on}$ and $T_{off}$ of the ultrasound generating means 13, the amount of liquid ejected by the liquid droplet spray device may be controlled.

Figure 2:
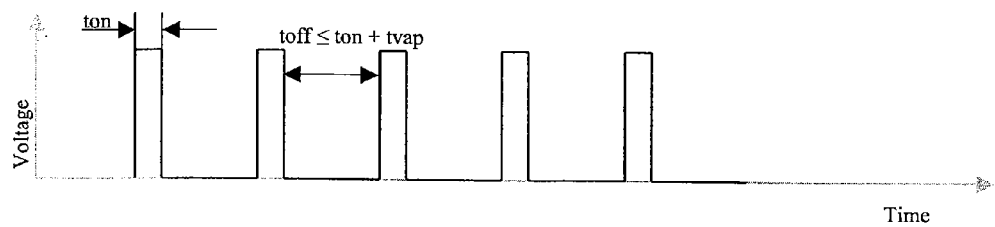
FIG. 2 shows an example of a pulsed drive signal for driving an ultrasound generating means in a liquid droplet spray device according to the present invention.

The total duration of operation for expelling a predetermined amount of liquid is thus $T=T_{on}+T_{off}$. An example of a drive signal for actuating the ultrasound generating means is shown in FIG. 2.

Indeed, it has been found that by using a pulsed drive of the ultrasound generating means in a particularly advantageous way, a more efficient operation may be obtained thus resulting in a reduced power consumption of the liquid droplet spray device while eliminating or minimising fall-back.

By further adjusting the energy supplied to the ultrasound generating means, the amount of expelled droplets can also be influenced. Basically, more energy input means that more droplets will be expelled.

This energy adjustment relates to the on and off time, $T_{on}$ and $T_{off}$ as well as to the amplitude of a pulsed drive signal of the electronic control means. The longer $T_{on}$ during which the ultrasound generating means is actuated, the more energy is provided and thus the more droplets are expelled during a period T. $T_{on}$ will be chosen to obtain a maximum height of the sprayed cloud of droplets for a given liquid. By also controlling the off time $T_{off}$ i.e. by controlling the distance in time of the driving signal, the height of the expelled spray cloud can be controlled.

In fact, $T_{on}$ consists of $T_{ona}$ and $T_{onb}$, where $T_{ona}$ is the time required to ultrasonically energise the liquid, and $T_{onb}$ is the time to spray the liquid. $T_{ona}$ may last from less than 1 second to several seconds. As will be explained further, both $T_{ona}$ and $T_{onb}$ contribute to generate a maximum height of the sprayed cloud of droplets for a given liquid.

It was found that if too many droplets are expelled, i.e. if the number of sequences of sprays of droplets expelled are in quick succession, i.e. $T_{off}$ is relatively small compared to $T_{on}$, the ejected sprays tend towards becoming a large and dense cloud, as the earlier expelled droplets will not yet have fully evaporated before newly expelled droplets arrive. The droplets may then interfere with each other, thus possibly preventing each other from fully evaporating before falling back to the surface surrounding the spray device and thus leading to a certain amount of fallback.

On the other hand, if $T_{off}$ is increased with respect to $T_{on}$, for a same period T, the hovering cloud of expelled droplets is much less dense and the droplets may all evaporate before falling back to the surrounding surface.

Indeed, it has been found that by measuring the evaporating time $T_{evap}$ that is required for a sprayed cloud of a given liquid produced during $T_{on}$ to fully evaporate, and by controlling the time $T_{off}$ so as to be longer than $T_{evap}$, fallback can be effectively controlled.

Thus, by controlling the ratio between $T_{off}$, $T_{on}$ and $T_{evap}$ the fallback may be further avoided.

Indeed, it has been found that $T_{off} \geq T_{on} + T_{evap}$.

For example, for a given liquid having a viscosity of 4 cps, $T_{on}$=50 ms, $T_{evap}$=950 ms, and thus $T_{off}$ is at least 1 sec.

For some liquids, like glycerine or aqueous solutions of glycerine, where the viscosity at 30° C. may be higher than 30 cps, for example 33.9 cps at a concentration of 80% glycerine in water ($H_2O$), it may be an advantage to use the energy produced by the ultrasound generating means to heat this aqueous solution during a short period of time from ambient to 80° C. where the viscosity of the solution will drop to 5.13 cps and where it can be dispensed as droplets easily.

As said before, $T_{on}$ therefore consists of $T_{ona}$ and $T_{onb}$, where $T_{ona}$ is the time required to ultrasonically energise the liquid in the way described above, and $T_{onb}$ is the time to spray the liquid. Thus, a maximum height of the sprayed cloud of droplets for the solution can be reached by lowering the flow resistance of the liquid $T_{ona}$ and then dispensing it during $T_{onb}$.

$T_{ona}$ may last from less than tens of milliseconds to 1 second and to several seconds depending on the liquid and the volume to be energized and sprayed to a maximum height of the sprayed cloud of droplets for a given liquid.

It is known that the viscosity of a liquid changes with the temperature. It is therefore desirable to allow adjusting the operation of the ultrasound generating means to adapt to the temperature change so as to ensure correct operation of the liquid droplet spray device, and thus to minimise fall-back, even with varying ambient temperature, and varying viscosities.

In this respect, it should be noted that the present Applicant has conceived an electronic control system for a liquid droplet spray device that allows such adjustment. This has been described in co-pending application EP 07 118 212.5. For example, due to ambient temperature changes, the liquid droplet spray device might operate at a different frequency in a more efficient manner, so that by checking an envelope of a system response signal, the new peak can be detected which thus gives the new optimum operating frequency.

Further, memory means may be provided for storing parameters from the ultrasound generating means. Upon fabrication, several parameters may be measured, and then stored, for different ambient temperatures. Thus, physical characteristics of the ultrasound generating means at different temperatures may be stored. Likewise, reference characteristics at different temperature and for different viscosities may be stored. Once the liquid droplet spray device is activated, the optimum operating frequency is determined. This frequency will thus correspond to a certain ambient temperature.

By comparing the frequency with one pre-stored in the memory means, it is thus possible to determine the corresponding ambient temperature, as explained in detail in the above-mentioned co-pending application.

It should be noted that such memory means may also store information relating to liquids to be used for spraying by the liquid droplet spray device. For example, for several perfumes, a certain viscosity at a certain temperature may also be pre-stored.

It is thus possible to operate the liquid droplet spray device at the determined optimum operating frequency, for the given ambient temperature, and possibly also for a given viscosity of a liquid to be sprayed.

By using a periodic monitoring, it is possible to ensure a correct operation of the liquid droplet spray device with time. Thus, even if there is a temperature change, the operating frequency of the atomiser is further controlled to remain at an optimum operating frequency. As such, also the fallback can be controlled even with a varying ambient temperature.

Figure 3:
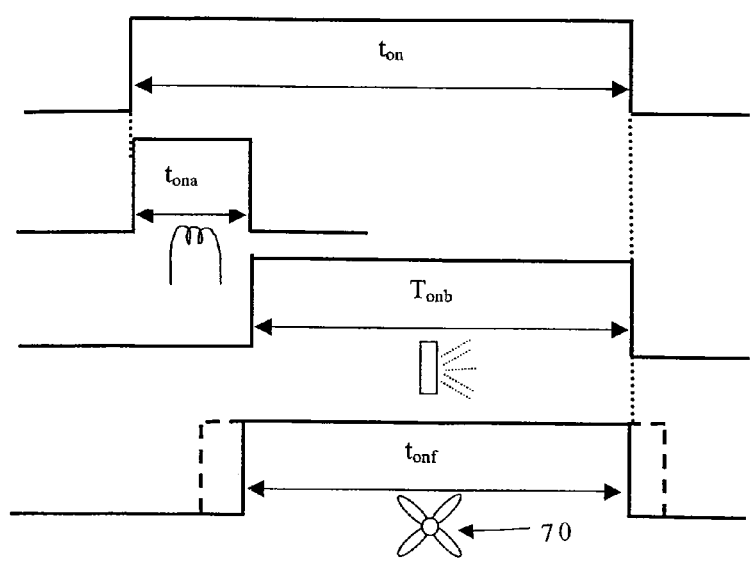
FIG. 3 shows in more detail the relative durations of timings $T_{ona}$, $T_{onb}$ and $T_{onf}$.

In some cases, it may be useful to further provide a fan 70 (See FIG. 3), which may be suitably arranged with respect to the membrane plate. For instance when spraying a dense cloud of relatively large droplets that may be close to or in excess of 10 μm in diameter, for example, it may be necessary to operate a fan 70 at least temporarily in order to increase the lift height of the cloud. In such case it may be advantageous to adapt the timing of the fan operation $T_{onf}$ with respect to $T_{onb}$ as shown in FIG. 3. $T_{onf}$ starts preferably a few tens of milliseconds, for example 50 ms, before $T_{onb}$ starts, and also lasts a few milliseconds longer than $T_{onb}$, for example also 50 ms. This allows accelerating the expelled cloud and thus to increase the lift height as well as avoiding the fall back of heavier droplets at the end of $T_{onb}$.

Having described now the preferred embodiments of this invention, it will be apparent to one of skill in the art that other embodiments incorporating its concept may be used. It is felt, therefore, that this invention should not be limited to the disclosed embodiments, but rather should be limited only by the scope of the appended claims.

The invention claimed is:

1. A method of controlling evaporation of droplets of a liquid nebulised as a spray of droplets from a liquid droplet spray device, wherein said liquid droplet spray device comprises a reservoir for containing the liquid, a perforate membrane plate, fluid interface means for feeding the liquid from the reservoir to the membrane plate, ultrasound generating means arranged to act on the supplied liquid to cause the liquid to vibrate and to be expelled as a spray of droplets through orifices of the membrane plate, and electronic control means for controlling activation of the ultrasound generating means, wherein the method comprises the steps of:

(a) providing the liquid droplet spray device;

(b) supplying the liquid to a space below the perforated membrane plate;

(c) providing a pulsed driving signal having a period T for activating the ultrasound generating means;

(d) activating the ultrasound generating means for a period of time $T_{on}$ so the ultrasound generating means acts on the liquid and vibrates the liquid so as to cause the spray of droplets to be expelled at a maximum spray cloud height, wherein $T_{on}$ consists of $T_{ona}$ and $T_{onb}$, and wherein vibration of the liquid by the ultrasound generating means heats the liquid;

(e) de-activating the ultrasound generating means for a period of time $T_{off}$, where $T_{off} \geq T_{on} + T_{evap}$, wherein $T_{evap}$ is the time required for the sprayed cloud of a given liquid produced during $T_{on}$ to fully evaporate, and wherein $T_{ona}$ is the time required to ultrasonically heat the liquid, $T_{onb}$ is the time to spray the liquid, and $T_{ona}$ lasts from less than tens of milliseconds to several seconds, whereby an amount of unevaporated liquid that falls back on a surface surrounding the liquid droplet spray device is minimised.

2. A method according to claim 1, wherein $T_{off} > T_{on} + T_{evap}$.

3. A method according to claim 1, further comprising the step of:

(f) providing a fan, wherein said fan is activated for a time $T_{onf}$ and where $T_{onf}$ starts several milliseconds before $T_{onb}$ and lasts several milliseconds longer than $T_{onb}$.

4. A liquid droplet spray device for nebulising a liquid expelled from the liquid droplet spray device, the liquid droplet spray device comprising:

(a) a reservoir for containing the liquid;

(b) a perforate membrane plate;

(c) a space for containing liquid to be expelled, wherein the space is positioned adjacent the membrane plate and is arranged to receive liquid from the reservoir;

(d) fluid interface means for feeding the liquid from the reservoir to the space;

(e) ultrasound generating means arranged to act on supplied liquid to cause the liquid to vibrate and to be expelled as a spray of droplets through orifices of the membrane plate; and (f) electronic control means for controlling activation of the ultrasound generating means, wherein the electronic control means is configured to drive the ultrasound generating means with a pulsed driving signal having a period T, wherein the electronic control means is configured to activate the ultrasound generating means for a period of time $T_{on}$ so the ultrasound generating means acts on the liquid so as to vibrate the liquid and cause a spray of droplets to be expelled at a maximum spray cloud height, wherein $T_{on}$ consists of $T_{ona}$ and $T_{onb}$, and wherein vibration of the liquid by the ultrasound generating means heats the liquid, wherein the electronic control means is configured to not to activate the ultrasound generating means (13) for a period of time $T_{off}$, where $T_{off} \geq T_{on} + T_{evap}$, wherein $T_{evap}$ is the time required for the sprayed cloud of a given liquid produced during $T_{on}$ to fully evaporate, and wherein $T_{ona}$ is the time required to ultrasonically heat the liquid, $T_{onb}$ is the time to spray the liquid, and $T_{ona}$ lasts from less than tens of milliseconds to several seconds, whereby an amount of unevaporated liquid that falls back on a surface surrounding the liquid droplet spray device is minimised.

5. A liquid droplet spray device according to claim 4, wherein $T_{off} > T_{on} + T_{evap}$.

6. A liquid droplet spray device according to claim 4, wherein said electronic control means includes memory means for storing fabrication parameters of said ultrasound generating means.

7. A liquid droplet spray device according to claim 6, wherein said memory means further stores external parameters comprising ranges of viscosities of liquids at specific temperatures to be used with said liquid droplet spray device.

8. A liquid droplet spray device according claim 4, wherein said fluid interface means are sized so that capillary action of said fluid interface means for a given viscosity is such that said space is filled in an optimal way in order to further reduce fall out.

9. A liquid droplet spray device according claim 4, further comprising a fan, wherein said fan is arranged to be activated for a time $T_{onf}$ where $T_{onf}$ starts several milliseconds before $T_{onb}$ and lasts several milliseconds longer than $T_{onb}$.

* * * * *